United States Patent [19]

Rossetti et al.

[11] 4,164,499

[45] * Aug. 14, 1979

[54] RIFAMYCIN COMPOUNDS

[75] Inventors: Vittorio Rossetti; Leonardo Marsili; Carmine Pasqualucci, all of Milan, Italy

[73] Assignee: Archifar Laboratori Chimico Farmachologici S.p.A., Rovereto, Italy

[*] Notice: The portion of the term of this patent subsequent to Apr. 25, 1995, has been disclaimed.

[21] Appl. No.: 825,165

[22] Filed: Aug. 12, 1977

[30] Foreign Application Priority Data

Sep. 30, 1976 [IT] Italy .................. 5209 A/76

[51] Int. Cl.² ........................................... C07D 498/18
[52] U.S. Cl. ......................... 260/239.3 P; 424/273 R
[58] Field of Search .................... 260/239.3 P

[56] References Cited

U.S. PATENT DOCUMENTS

| | | | |
|---|---|---|---|
| 4,017,481 | 4/1977 | Marsili et al. | 260/239.3 P |
| 4,086,225 | 4/1978 | Marsili et al. | 260/239.3 P |

FOREIGN PATENT DOCUMENTS

| | | | |
|---|---|---|---|
| 1670479 | 1/1971 | Fed. Rep. of Germany | 260/239.3 P |
| 1670377 | 2/1974 | Fed. Rep. of Germany | 260/239.3 P |
| 2622638 | 12/1976 | Fed. Rep. of Germany | 260/239.3 P |

*Primary Examiner*—John M. Ford
*Assistant Examiner*—Robert T. Bond
*Attorney, Agent, or Firm*—Haseltine, Lake & Waters

[57] ABSTRACT

Rifamycin compounds having high antibacterial activity, comprising powders of red-violet color. Such compounds are obtained by reacting 3-aminosubstituted-4-desoxo-4-imino rifamycin S with linear and cyclic ketones.

1 Claim, No Drawings

RIFAMYCIN COMPOUNDS

This invention relates to novel rifamycin compounds having high antibacterial activity.

In German Patent Application DOS No. 1,670,479 laid open on Jan. 28, 1971 and in German Patent No. 1,670,377 granted February 28, 1974 derivatives of rifamycin S are described as having the formula:

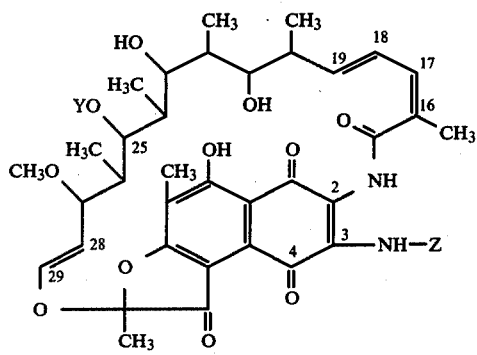

and 16, 17, 18, 19 tetrahydroderivatives and 16, 17, 18, 19, 28, 29 hexahydroderivatives thereof, wherein:

Y is —H or —COCH$_3$, and Z is, inter alia, an alkyl having 1 to 3 C atoms; cycloalkyl having 3 to 6 C atoms; phenyl; phenyl substituted with at least one radical selected from the group consisting of halogen and methyl.

The present applicants have synthetized rifamycin compounds having the formula:

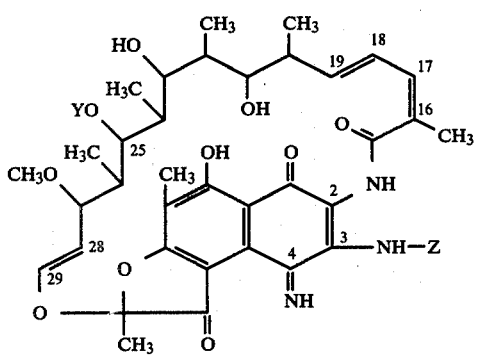

and 16, 17, 18, 19 tetrahydroderivatives and 16, 17, 18, 19, 28, 29 hexahydroderivatives thereof, wherein Y and Z are as above defined.

Such compounds of formula (II) are obtained by dissolving in a solvent selected from the group consisting of tetrahydrofuran and 1,4-dioxane a compound of formula (I), and reacting such a solution with ammonia gas at a temperature ranging between −10° C. and +35° C. for a time of 1 to 40 hours.

This invention relates to rifamycin compounds having the formula:

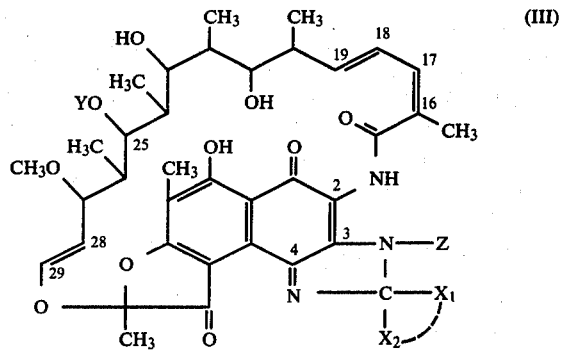

and 16, 17, 18, 19 tetrahydroderivatives and 16, 17, 18, 19, 28, 29 hexahydroderivatives thereof, wherein:

Y and Z are as those defined for formula (I),

X$_1$ is methyl,

X$_2$ is selected from the group consisting of an alkyl having 1 to 3 C atoms, carboxyalkyl having 3 or 4 C atoms, halogenmethyl, and X$_1$ and X$_2$ along with the C atom, to which they are bonded, form a ring selected from the group consisting of a ring having 5 or 6 C atoms, a heterocyclic ring of 6 members containing one heteroatom N, a heterocyclic ring of 6 members containing one heteroatom N and substituted on atom N with a radical selected from the group consisting of alkyl having 1 to 4 C atoms, cycloalkyl having 6 C atoms, and arylalkyl having 7 C atoms.

These compounds have high antibacterial activity on Gram-positive and Gram-negative bacteria, and particularly on Mycobacterium Tuberculosis. Such compounds are powders of red-violet colour, soluble in most of organic solvents, such as chlorinated solvents, alcohols, esters, ethers, and partially soluble in aromatic hydrocarbons.

The compounds of formula (III) can be obtained by dissolving a compound of formula (II) in an aprotic solvent selected from the group consisting of tetrahydrofuran, 1,4-dioxane and dimethyl sulphoxide, and reacting it, at a temperature ranging between 10° C. and 60° C. and for a time of 2–30 hours, with a ketone having the formula:

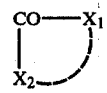

wherein X$_1$ and X$_2$ are those defined for formula (III), the reaction being carried out in the presence of a reducing metal selected from the group consisting of Zn and Fe and in the presence of an organic acid selected from the group consisting of formic acid and acetic acid. Since, as above discussed, the compound of formula (II) is obtained from the compound of formula (I), the compound of formula (III) can be directly obtained from the compound of formula (I) without isolating the compound of formula (II).

Compounds of a formula similar to those according to the present invention are described in German Patent Applications DOS No. 2,622,638 laid open on Dec. 9, 1976 and DOS No. 2,626,296 laid open on Dec. 30, 1976, but are distinguished from the latter in that nitrogen linked to C atom at position 3 carries an alkyl or aryl group.

In order that the present invention be more clearly understood, some exemplary embodiments thereof will now be described as given in not limiting sense. In the examples, chromatography studies on thin layer were carried out on silica gel plates Merck $F_{254}$ 5×10 cm, using the mixture benzene/ethyl acetate/methanol (20:7:8) as eluent.

I.R. spectra were carried out in suspension of vaseline oil (Nujol).

Electronic absorbing spectra were carried out in methanol solution.

EXAMPLE 1

10 g 3-anilino-4-desoxo-4-imino rifamycin S were dissolved in 150 ml acetone. The solution was cooled to 15° C., and under stirring 1 g powder zinc and 5 ml acetic acid were added. The colour of the reaction mixture changed to yellow-orange and then to red. The mixture was stirred at 15° C. overnight and filtered. The filtrate was diluted with 400 ml chloroform and 300 ml water were added, then stirring for 5 minutes and decanting. The organic layer was washed again with water and then dried on sodium sulphate, the solvent was evaporated at reduced pressure, and the residue, dissolved in 15 ml benzene was chromatographied on column containing 300 g silica gel, eluting with a mixture benzene/acetone (85:15). After fraction evaporation, a residue was obtained which upon crumbling with n-hexane yielded 3.6 g red crystalline product of formula (III), wherein $X_1$ and $X_2$ are methyl and Z is phenyl.

Rf=0.75

$\lambda_{max}=496$ nm ($E_{1cm}^{1\%}=43$)

I.R. 3450–3200, 1740, 1720(Sh), 1650(Sh), 1615, 1562, 1430, 1330, 1295, 1250(Sh), 1265, 1200, 1175–1165, 1125, 1080, 1020, 985–970, 950, 905 and 825 cm$^{-1}$.

The $^1$H NMR spectrum (CDCl$_3$) displays the following main absorptions: 0.08δ(d, CH$_3$—C(H)), 0.54–1.15δ(m, 3 CH$_3$—C(H)), 1.37, 1.52, 1.78, 1.87, 2.04 and 2.30δ

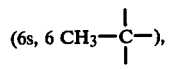

3.10δ(s, CH$_3$O), 5.0–7.0δ(m, C-25 and olefinic protons), 7.40δ(broad s, CH$_3$O). (TMS as int. standard). The $^{13}$C NMR spectrum (C$_6$D$_6$) shows a signal at 97.2 ppm (singlet in the off-resonance spectrum) attributable to the heterocyclic carbon atom and two signals at 23.7 and 23.8 ppm (quartets in the off-resonance spectrum) corresponding to the geminal methyl groups. (TMS as int. standard).

EXAMPLE 2

A solution obtained by dissolving 5 g 3-anilino-4-desoxo-4-imino rifamycin S in 25 ml tetrahydrofuran was reacted with 5 g powder zinc, 5 g 1-methyl-piperidone (4) and 50 ml acetic acid at 0° C. under normal stirring for 4 hours. After unreacted zinc filtering, the operation was carried out as in Example 1, thus obtaining a rubbery residue, therefrom isolating 250 mg pure product of formula (III), wherein $X_1$ and $X_2$ are bonded to each other to form a residue 4-piperidinilidene-1- methyl and Z is phenyl, by chromatography on column as in Example 1. Rf=0.37.

EXAMPLE 3

5 g 3-anilino-rifamycin S were dissolved in 50 ml tetrahydrofuran. Anhydrous ammonia was bubbled for 10 minutes into the solution cooled to 2° C.; and the reaction solution was allowed to rest at 10° C. for 5 hours. Excessive ammonia was then removed under vacuum, and 2 g powder zinc, 5 ml cyclohexanone and 10 ml formic acid at 15° C. were added under stirring. The reaction mixture was stirred overnight at 15° C. and the unreacted zinc was filtered, the filtrate stirred with 30 ml aqueous solution of sodium sulphite for 10 minutes, then diluting with 200 ml chloroform and 200 ml water, and decanting. The organic layer was washed again with water and dried on sodium sulphate, the solvent was evaporated under vacuum and the residue chromatographied as described in Example 1 to yield 2.5 g red crystalline product of formula (III), wherein $X_1$ and $X_2$ are together cyclohexylidene and Z is phenyl.

Rf=0.73

I.R. 3475–3275, 1735, 1655, 1610, 1565, 1500(Sh), 1420, 1300, 1265, 1220(Sh), 1175, 1160, 1070, 970, 945, 895 and 815 cm$^{-1}$.

$\lambda_{max}=276$ nm ($E_{1cm}^{1\%}=349$), 316 nm ($E_{1cm}^{1\%}=187$), 490 nm ($E_{1cm}^{1\%}=47$).

EXAMPLE 4

5 g 3-anilino-4-desoxo-4-imino-rifamycin S were dissolved in 50 ml tetrahydrofuran. The solution was cooled to 10° C., and under stirring 5 g powder iron, 1.5 ml N-benzyl-piperidone(4) and 5 ml acetic acid were added. Stirring was continued at room temperature for 24 hours and the mixture was filtered. The filtrate was dropped in 250 ml water containing 10 g vitamin C. A rubbery solid was separated and dissolved in 200 ml chloroform. The chloroform solution was washed twice with 100 ml 5% solution of vitamin C and twice with 100 ml buffer phosphate at pH 7.4. After anhydrification and solvent removal under vacuum, the residue was dissolved in 15 ml benzene and purified by chromatography on silica gel column as described in Example 1. Thus, 1.5 g pure product of formula (III) were obtained, wherein $X_1$ and $X_2$ are together 4-piperidinilidene-1-benzyl and Z is phenyl.

Rf=0.7

I.R. 3425–3300, 1735, 1650, 1608, 1565, 1500(Sh), 1420, 1325, 1300, 1268, 1220, 1200, 1170–1160, 1100–1020, 975, 948, 895 and 805 cm$^{-1}$.

$\lambda_{max}=275$ nm ($E_{1cm}^{1\%}=300$), 316 nm ($E_{1cm}^{1\%}=153$), 496 nm ($E_{1cm}^{1\%}=35$).

EXAMPLE 5

5 g 3-(o-toluidino)-rifamycin S dissolved in 50 ml tetrahydrofuran were reacted with ammonia gas at 0° C. for 10 minutes. After ammonia flow shut off, the reaction mixture was allowed to stand for 2 hours and the temperature to rise to room temperature. Excessive ammonia was removed under vacuum and under stirring 1.5 g powder zinc, 1.5 ml methyl-ethyl-ketone and 10 ml acetic acid were added. The reaction was continued overnight under stirring and the insoluble fraction was filtered. The filtrate was diluted with chloroform and the obtained solution was repeatedly washed with water, finally anhydrifying and evaporating the solvent at reduced pressure, obtaining a residue that, dissolved in 15 ml benzene, was percolated on a column of 250 g silica gel, eluting with the mixture benzene/acetone (85:15). Thus, 2.2 g red crystalline product of formula (III) were obtained, wherein $X_1$ is methyl, $X_2$ is ethyl and Z is 2-tolyl.

Rf=0.77

I.R. 3300, 1740, 1655, 1610, 1565, 1500, 1420, 1328, 1303, 1270, 1250, 1230, 1195, 1180, 1170, 1125, 1075, 1020, 1000, 973, 945, 890, 840 and 810 cm$^{-1}$.

Elementary analysis for: $C_{48}H_{59}N_3O_{11}$

|  | C | H | N |
|---|---|---|---|
| Calculated, % | 67.51 | 6.96 | 4.92 |
| Found, % | 67.41 | 6.72 | 5.03 |

$\lambda_{max} = 277$ nm ($E_{1cm}^{1\%} = 351$), 320 nm ($E_{1cm}^{1\%} = 206$), 504 nm ($E_{1cm}^{1\%} = 45$).

EXAMPLE 6

5g 3-(o-toluidino)-4-desoxo-4-imino-rifamycin S were dissolved in 50 ml tetrahydrofuran and at room temperature and under stirring 1.5 g powder zinc, 1.5 ml 1-benzyl-piperidone(4) and 10 ml acetic acid were added, taking care of not allowing a rise in temperature beyond 25° C. AFter reaction for 15 hours, the solution was filtered. By acting as described in the preceding examples, a raw product was isolated which, chromatographied on column as above described, yielded 0.95 g pure product of formula (III), wherein $X_1$ and $X_2$ are together 4-piperidinilidene-1-benzyl and Z is 2-tolyl.

Rf=0.77

I.R. 3450, 3300, 1730, 1665(Sh), 1650, 1605, 1560, 1490(Sh), 1420, 1300, 1260, 1225, 1200, 1165, 1145, 1125, 1105, 1080, 1060, 1010, 995, 980, 900 and 810 cm$^{-1}$.

Elementary analysis for: $C_{56}H_{66}N_4O_{11}$

|  | C | H |
|---|---|---|
| Calculated, % | 69.26 | 6.85 |
| Found, % | 68.81 | 6.47 |

$\lambda_{max}=277$ nm ($E_{1cm}^{1\%}=314$), 315 nm ($E_{1cm}^{1\%}=180$), 492 nm ($E_{1cm}^{1\%}=43$).

EXAMPLE 7

5 g 3-(p-chloroanilino)-rifamycin S were dissolved in 50 ml tetrahydrofuran; ammonia was bubbled at 3° C. Under stirring at 19° C., 2 g powder zinc, 5 ml cyclopentanone and 10 ml acetic acid were added. After stirring overnight at room temperature, the solution was heated to 40° C. for 10 hours and filtered. The filtrate was treated as above described and the raw product thus obtained was purified by percolation on column with silica gel, eluting with benzene/acetone (85:15). Thus, 0.25 g product of formula (III) were obtained, wherein $X_1$ and $X_2$ are together cyclopentylidene and Z is 4-chloro-phenyl.

Elementary analysis for: $C_{48}H_{56}N_3O_{11}$

|  | C | H | N |
|---|---|---|---|
| Calculated, % | 65.04 | 6.37 | 4.74 |
| Found, % | 65.47 | 6.30 | 4.24 |

EXAMPLE 8

5 g 3-(o-toluidino)-4-desoxo-4-imino-rifamycin S were dissolved in 50 ml tetrahydrofuran and at room temperature 2 g powder zinc, 5 ml ethyl acetoacetate and 10 ml acetic acid were added. After reacting for 24 hours, the solution was filtered and acting as described in the preceding examples, a solid was isolated and crumbled with 30 ml boiling acetone. After cooling and filtering, the filtrate was concentrated to a reduced volume and chromatographied on silica gel (eluent: benzene/acetone 85:15), thus yielding 0.2 g product of formula (III), wherein $X_1$ is methyl, $X_2$ is methyl-ethyl-carboxylate and Z is 2-tolyl.

Rf=0.80

I.R. 3450, 3300(Sh), 1740, 1650, 1610, 1565, 1485(Sh), 1420, 1330, 1300, 1265, 1220, 1195, 1175, 1165, 1060, 970, 945, 895, 840 and 810 cm$^{-1}$.

$\lambda_{max}=274$ nm ($E_{1cm}^{1\%}=300$), 317 nm ($E_{1cm}^{1\%}=167$), 498 nm ($E_{1cm}^{1\%}=35$).

EXAMPLE 9

4.1 g 3-cyclopropylamino-rifamycin S were dissolved in 50 ml tetrahydrofuran and such a solution was cooled to 10° C. Then, ammonia gas was bubbled for 4 hours, while holding the temperature between 5° and 10° C. Excessive ammonia was removed under vacuum and then, under stirring, 2 g 1-methyl-piperidone(4), 2 g powder zinc and 5 ml acetic acid were added at 15° C. At room temperature, the reaction was continued overnight and then the mixture was filtered. The filtrate was diluted with 100 ml chloroform and this solution was repeatedly washed with water, then anhydrified and solvent was removed at reduced pressure. The residue thus obtained was dissolved in 20 ml methanol and then diluted with 100 ml benzene: by water addition, a solid was separated, filtered and discarded. The mother liquors were allowed to decant and the aqueous layer was discarded. The benzene solution was washed twice with 100 ml 10% aqueous solution of citric acid, the aqueous layers were combined and extracted five times with 50 ml chloroform. As combined and anhydrified, the chloroform solutions were dry evaporated. Thus, a residue was obtained that was treated with ethyl ether and filtered. After stove drying, 2.5 g brick-red crystalline product of formula (III) were obtained, wherein $X_1$ and $X_2$ are together 4-piperidinilidene-1-benzyl and Z is cyclopropyl.

Rf=0.31

I.R. 3300, 1720, 1645, 1605, 1565, 1417, 1297, 1255, 1180, 1160, 1058, 1045, 1005, 968, 953, 890, 835 and 808 cm$^{-1}$.

$\lambda_{max}=273$ nm ($E_{1cm}^{1\%}=296$), 312 nm ($E_{1cm}^{1\%}=164$), 488 nm ($E_{1cm}^{1\%}=30$).

EXAMPLE 10

4 g 3-cyclopropylamino-4-desoxo-4-imino-rifamycin S were reacted in 50 ml tetrahydrofuran with 2 ml cyclohexanone, 2 g powder zinc and 10 ml acetic acid at room temperature for 24 hours. The unreacted zinc was filtered and a dilution was carried out with 100 ml chloroform. The solution was repeatedly washed with water, the solvent was evaporated at reduced pressure and 150 ml ethyl ether were added. The insoluble fraction was filtered and the filtrate was added with 50 ml water containing 2.5 g vitamin C and under stirring pH of the aqueous layer was brought to 7.5 with 3% sodium carbonate. After decanting, the aqueous layer was discarded. This operation was repeated for other two times and finally the ether layer was anhydrified on magnesium sulphate, then concentrating to about 30 ml. After 3 days at 5° C., the product was completely crystallized, then filtered and washed with ether. Thus, 2.5 g product of formula (III) were obtained, wherein $X_1$ and $X_2$ are together cyclohexylidene and Z is cyclopropyl.

Rf=0.76

I.R. 3525, 3450, 3200, 1740, 1725, 1655, 1650, 1560, 1420, 1300, 1260, 1230, 1180, 1130, 1090, 1065, 1028, 975, 948, 925, 910, 845, 825 and 810 cm$^{-1}$.

$\lambda_{max}$=273 nm ($E_{1cm}^{1\%}$=364), 318 nm ($E_{1cm}^{1\%}$=187), 468 nm ($E_{1cm}^{1\%}$=50).

The same reaction could be effected by using dimethyl sulphoxide as a solvent, obtaining the same product.

EXAMPLE 11

0.6 g 3-cyclopropylamino-4desoxo-4-imino-rifamycin S were dissolved in 20 ml acetone, and 0.1 g powder zinc and 1 ml acetic acid were added. Stirring of the reaction mixture was continued for 3 days at room temperature. The unreacted zinc was filtered and the filtrate diluted with 50 ml chloroform, the solution was washed with water and the solvent removed at reduced pressure. Thus, a residue was obtained that was treated with 50 ml benzene to ebullition, and after cooling the product was filtered. The solid was discarded and the filtrate concentrated to reduced volume. By dilution with isopropyl ether, a red product crystallized which, upon filtering and drying, weighed 0.2 g and comprised a compound of formula (III), wherein $X_1$ and $X_2$ are methyl and Z is cyclopropyl.

Rf=0.61.

What we claim is:

1. A rifamycin compound having the formula

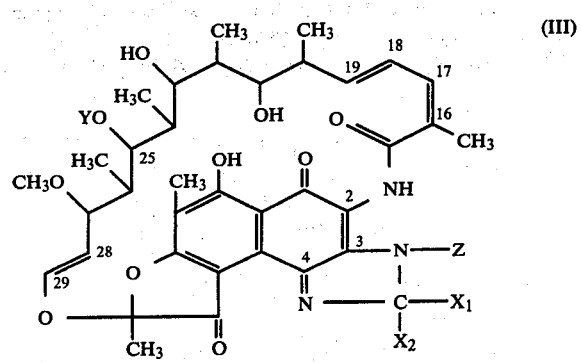

and 16, 17, 18, 19 tetrahydroderivatives and 16, 17, 18, 19, 28, 29 hexahydroderivatives thereof, wherein:

Y is selected from the group consisting of —H and —COCH$_3$;

Z is selected from the group consisting of alkyl having 1-3 carbon atoms, cycloalkyl having 3-6 carbon atoms and phenyl substituted with one radical selected from the group consisting of halogen and methyl;

$X_1$ is methyl;

$X_2$ is selected from the group consisting of alkyl having 1-3 carbon atoms, carboxyalkyl having 3 or 4 carbon atoms, and halomethyl; or $X_1$ and $X_2$, when taken with the atom of carbon to which they are attached, form a ring selected from the group consisting of a cycloalkyl ring having 5 or 6 carbon atoms, a piperidine ring and an N-substituted piperidine ring, the nitrogen atom being in the 4-position of said unsubstituted or N-substituted piperidine ring with respect to the spiro C-atom, said substituent selected from the group consisting of alkyl having 1-4 carbon atoms, cycloalkyl having 6 carbon atoms and benzyl.

* * * * *